(12) United States Patent
Davis et al.

(10) Patent No.: US 7,393,459 B2
(45) Date of Patent: Jul. 1, 2008

(54) METHOD FOR AUTOMATIC DETERMINATION OF SUBSTRATES STATES IN PLASMA PROCESSING CHAMBERS

(75) Inventors: Matthew F Davis, Brookdale, CA (US); Lei Lian, Santa Clara, CA (US); Quentin E. Walker, Palo Alto, CA (US)

(73) Assignee: Applied Materials, Inc., Santa Clara, CA (US)

( * ) Notice: Subject to any disclaimer, the term of this patent is extended or adjusted under 35 U.S.C. 154(b) by 547 days.

(21) Appl. No.: 10/939,158

(22) Filed: Sep. 10, 2004

(65) Prior Publication Data

US 2006/0028646 A1 Feb. 9, 2006

Related U.S. Application Data

(60) Provisional application No. 60/599,515, filed on Aug. 6, 2004.

(51) Int. Cl.
G01L 21/30 (2006.01)
H01L 21/66 (2006.01)

(52) U.S. Cl. ............................. 216/59; 216/60; 438/14; 438/16

(58) Field of Classification Search ................... 216/59, 216/60; 438/14, 16
See application file for complete search history.

(56) References Cited

U.S. PATENT DOCUMENTS

| | | | |
|---|---|---|---|
| 5,536,359 A * | 7/1996 | Kawada et al. ................ | 438/16 |
| 6,419,846 B1 | 7/2002 | Toprac et al. | |
| 6,521,080 B2 | 2/2003 | Balasubramhanya et al. | |
| 6,566,270 B1 * | 5/2003 | Liu et al. ..................... | 438/706 |
| 6,829,056 B1 * | 12/2004 | Barnes et al. ................ | 356/625 |
| 2002/0119660 A1 * | 8/2002 | Sarfaty et al. ............... | 438/689 |
| 2003/0192864 A1 * | 10/2003 | Tanaka et al. .......... | 219/121.43 |
| 2004/0084406 A1 * | 5/2004 | Kamp et al. .................. | 216/59 |

FOREIGN PATENT DOCUMENTS

JP WO 03/077303 A1 * 9/2003

OTHER PUBLICATIONS

Yue, et al., "Plasma etching endpoint detection using multiple wavelengths for small open-area wafers," J. Vac. Sci, Technol. A, 19(1), Jan./Feb. 2001, 66-75.

* cited by examiner

*Primary Examiner*—Shamim Ahmed
(74) *Attorney, Agent, or Firm*—Patterson & Sheridan, LLP

(57) ABSTRACT

A method for automatic determination of a state of a substrate in a plasma processing chamber is provided. Substrate reflectance data is collected in a processing chamber prior to processing to be analyzed with reference reflectance data to determine if the substrate state meets a control criterion. The substrate state may define the thickness and the qualities of the films on the substrate, the critical dimensions of the different layers on the substrate. The reflectance data is analyzed using a multi-variant analysis technique, such as principle component analysis. In addition to analyzing substrate state prior to processing, substrate reflectance could also be collected in a processing chamber during processing to be analyzed with reference reflectance data to further determine if the substrate state and/or the substrate processing are meeting a control criterion.

27 Claims, 9 Drawing Sheets

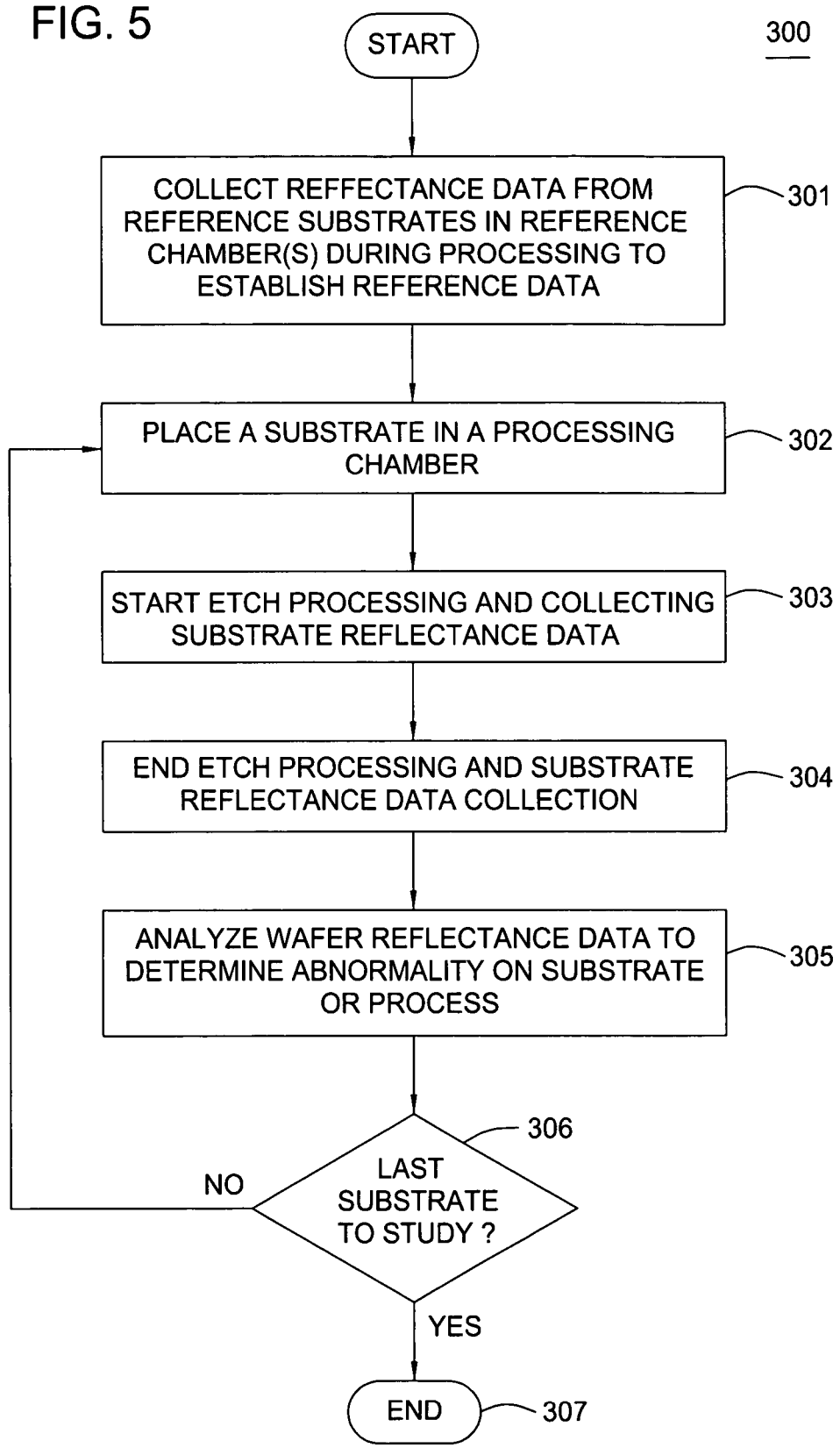

METHOD FOR AUTOMATIC DETERMINATION OF SUBSTRATES STATES IN PLASMA PROCESSING CHAMBERS

CROSS-REFERENCE TO OTHER APPLICATIONS

This application claims benefit of U.S. provisional patent application Ser. No. 60/599,515, filed Aug. 6, 2004, which is herein incorporated by reference.

BACKGROUND OF THE INVENTION

1. Field of the Invention

The present invention relates to semiconductor or flat panel substrate processing systems. More particularly, the present invention relates to techniques and apparatus for automatically determining the substrates states in semiconductor processing chambers.

2. Description of the Related Art

Within the semiconductor industry, an ever present need exists for improved process repeatability and control. As new generations of integrated circuits employ smaller feature sizes than were contemplated in previous generations, greater demands are placed on the integrated circuit fabrication process. Deposition and etching one or more layers of a semiconductor substrate in a plasma environment are two of the most common steps in integrated circuit manufacturing. To ensure that a correct quantity and quality of film is deposited or etched, the plasma state of the process chamber needs to be monitored comprehensively prior to, during and after production substrate processing.

During a plasma process, certain plasma "attributes", such as the plasma's optical electromagnetic emissions, the RF power delivered to a wafer pedestal, wafer reflectance (WR) (or substrate reflectance), process pressure and process temperature, manifest low frequency fluctuations that contain significant information about the plasma process and the plasma chamber. The intensity of a plasma's optical electromagnetic emission (OES), the fluctuations of the RF power delivered to a wafer pedestal, and the substrate reflectance (SR) during plasma processing contain information related to process state, process event and process chamber. OES, RF, and substrate reflectance states are affected to different degrees by varying chamber conditions and by process parameter changes. OES, RF, and substrate reflectance data are complementary to one another. Inclusion of these data during process or chamber monitoring is more comprehensive than merely including one of the three types of data. Details of how a chamber and process can be monitored during process to detect endpoint and fault have been disclosed in commonly assigned U.S. Pat. No. 6,368,975, entitled "Method and Apparatus For Monitoring A Process By Employing Principle component Analysis", issued on Apr. 9, 2002, its divisional application Ser. No. 10/341,696, filed on Jan. 14, 2003, and U.S. patent application Ser. No. 10/628,001, entitled "Method For Automatic Determination of Semiconductor Plasma Chamber Matching and Source of Fault by Comprehensive Plasma Monitoring," filed on Jul. 25, 2003, each of these patent and patent applications are incorporated by reference herein in their entireties.

At various stages of semiconductor or flat panel display substrate processing, substrates have different layers of materials on top. These different layers of materials have different thickness in each layer, which could be patterned to have different pattern densities and different critical dimensions (CDs). Some layers on the substrate could be doped with different dopants. The various materials on the substrates contribute to the state of the substrate (or substrate state). At various steps of substrate processing, incorrect processing or mis-processing could occur which could make the substrate fall out of the control limit. A substrate could receive too much deposition, which results in a film being too thick, or the deposition condition is not optimal, which results in a film with poor quality. Photolithography processing could have drifted to result in poor critical dimensions (CDs) on the substrate, i.e., the CDs are too small or too large. Poor etching processing could also affect critical dimensions (CDs). For the advanced processing in modern IC manufacturing, detecting substrates with previous processing steps out of specification is very important, since process drift could be interrupted to cause further mis-processing and also substrates that have already been mis-processing could either be reworked or be scratched to prevent further loss of manufacturing resources.

Therefore, there is a need in the art for techniques for automatically determining the state of a substrate in a processing chamber to determine if the substrate suffers mis-processing prior to or during processing in the process chamber.

SUMMARY OF THE INVENTION

The invention relates to a method for evaluating the state of a substrate prior to and during substrate processing. The results of the evaluation can be used to identify substrates that are not within specification and to notify system operators of the systems that might have caused the substrate to have attributes that are not within the specification. Such notification is useful to avoid further mis-processing of the substrate. One embodiment of the invention provides a method of evaluating a state of a substrate in a processing chamber comprises (a) collecting substrate reflectance data from at least one reference substrate to establish reference data, (b) placing a substrate in a processing chamber, (c) collecting substrate reflectance spectrum data, and (d) analyzing collected data to determine if the substrate state meets a control criterion.

Another embodiment of the invention further provides a method of evaluating a state of a substrate in an etch processing chamber comprises (a) collecting substrate reflectance data from at least one reference substrate to establish reference data, (b) placing a substrate in an etch processing chamber, (c) collecting substrate reflectance spectrum data, and (d) analyzing collected data to determine if the substrate state meets a control criterion.

BRIEF DESCRIPTION OF THE DRAWINGS

So that the manner in which the features of the invention described herein are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 5 shows a process of evaluating the state of a substrate in a process chamber during processing.

DETAILED DESCRIPTION

Certain substrate attributes, such as substrate reflectance, contain significant information about a state of the substrate (or substrate state). These substrate attributes can be analyzed to reveal the processing history of the substrate.

Figure 1:
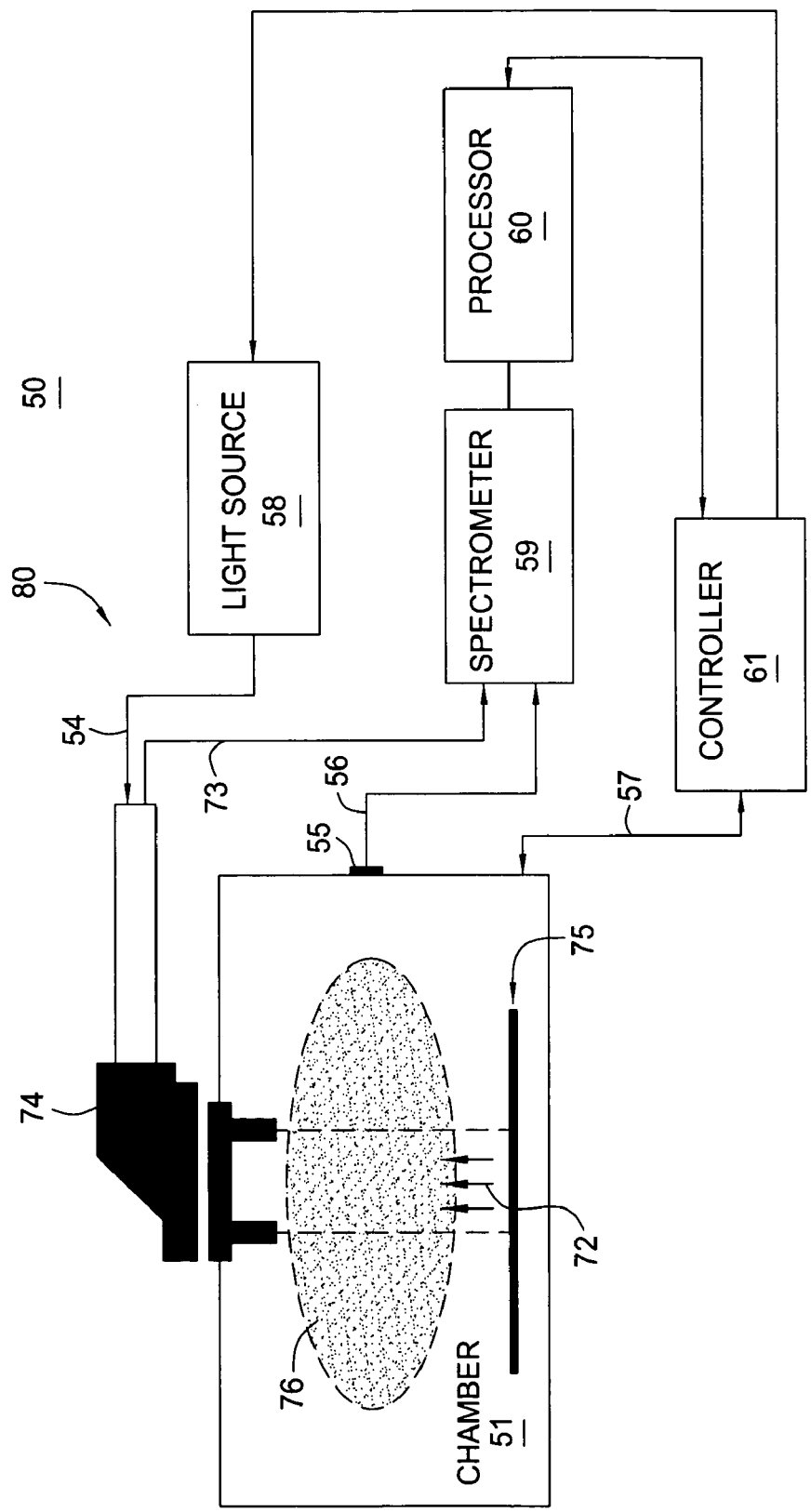
FIG. 1 is a schematic diagram of a substrate processing system comprising an optical spectrum collection and analysis apparatus.

The embodiments of the present invention can be used with any process chamber in which a spectrometer or other type of radiation collector can be either placed within the chamber to measure radiation reflected from the surface of the substrate or that includes a window or view port through which such radiation can be directed to a spectrometer located external to the chamber. FIG. 1 is a simplified cross-sectional view of an exemplary plasma chamber module 50 configured to practice one embodiment of the present invention. In one exemplary embodiment, the module comprises an in-situ metrology too. The in-situ metrology tool may be the EyeD™ metrology module, available from Applied Materials Inc., of Santa Clara, Calif. As shown in FIG. 1, the EyeD™ chamber module 50 comprises of three major components. One component is an interferometric and/or spectrometric measurement assembly 80, which comprises a beam-forming optics 74, a signal cable 73, a spectrometer 59, a processor 60, an optional broadband light source 58, and an optional fiber optic cable 54, to measure the film quality, the film thickness and/or the width of structures. The second component is an optical electromagnetic emission (OES) monitor assembly, which comprises an OES signal collecting device 55, a signal cable 56, the spectrometer 59 and the processor 60, to monitor the chamber plasma state. The third component is a RF sensor (not shown) capable of detecting changes of RF power delivered to the substrate pedestal.

The interferometric and/or spectrometric measurement assembly 80 may be, for example, configured to perform an interferometric monitoring technique (e.g., counting interference fringes in the time domain, measuring position of the fringes in the frequency domain, and the like) to measure the etch depth profile of the structures being formed on the substrate in real time. Light 72, reflected from a wafer 75, is collected by beam-forming optics 74 and the signals are transmitted by a signal cable 73 to a spectrometer 59. The signals are analyzed by the spectrometer 59 and a processor 60. The analyzed results can be used to generate control commands that control the reactor chamber via controller 61. If the assembly is used to control the endpoint of an etch process, it is called "interferometric endpoint" (IEP). External light from broadband light source 58, e.g., a mercury, deuterium or xenon lamp, could be employed to provide light through fiber optic cable 54 to the wafer. Such a light source may be used in addition to or instead of using the plasma as the light source. Details of film thickness measurement and control (or endpoint) by EyeD™ have been disclosed in commonly assigned U.S. Pat. No. 6,413,867, entitled "Film Thickness Control Using Spectral Interferometry", issued on Jul. 2, 2002, and U.S. application Ser. No. 10/286,402 entitled "Interferometric Endpoint Determination In A Substrate Etching Process", filed Nov. 1, 2002, both of which are incorporated herein by reference in their entireties. The interferometric and/or spectrometric measurement assembly may also use one or more non-destructive optical measuring techniques, such as spectroscopy, scatterometry, reflectometry, and the like, to measure the width of structures.

Figure 2:
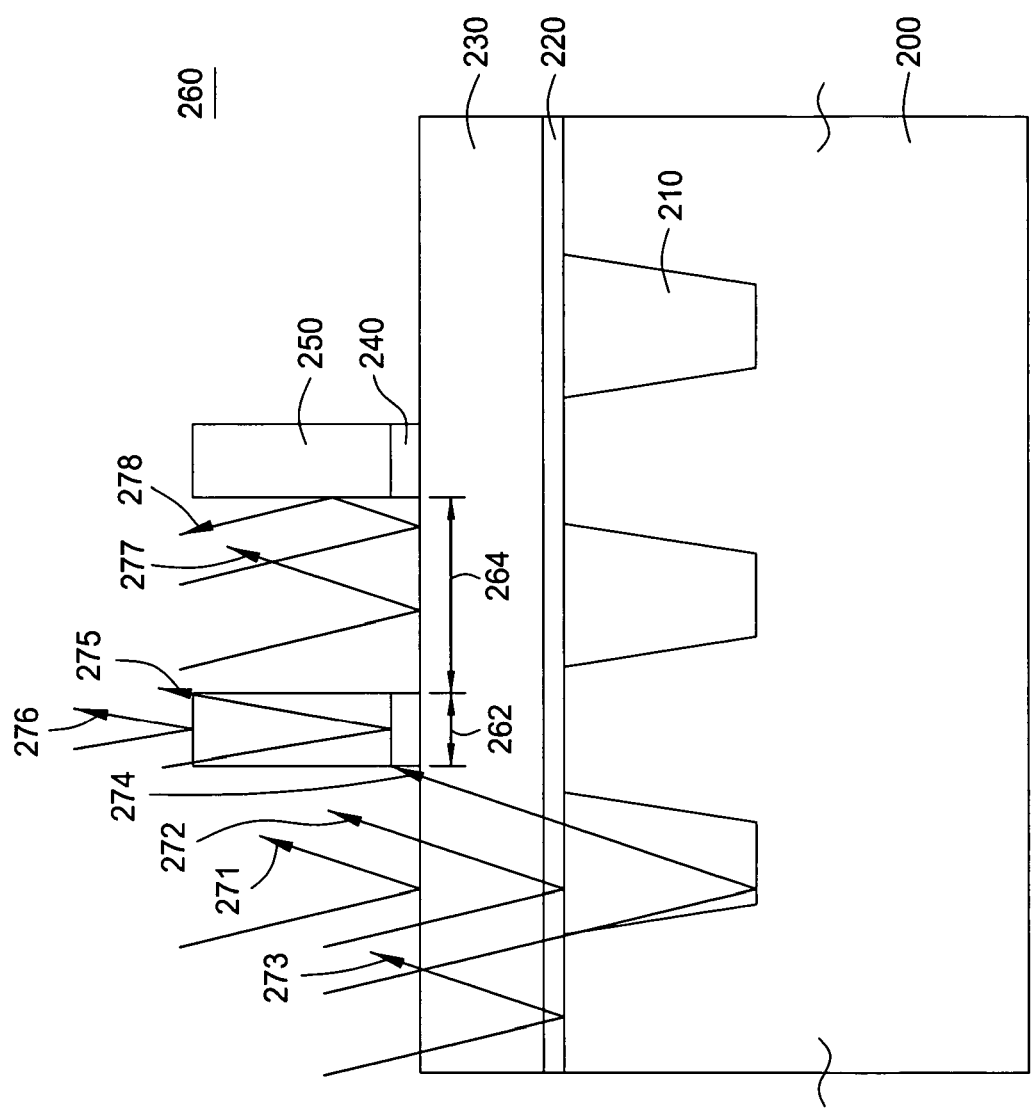
FIG. 2 shows a schematic cross-section of a substrate with shallow trench isolation (STI), gate dielectric, gate and patterning layers, and reflected light beams.

FIG. 2 shows the cross section of an exemplary substrate 260 that has a substrate material 200, shallow trench isolation (STI) 210, a thin dielectric layer 220, a polysilicon layer 230, an etched dielectric anti-reflective coating layer (DARC) layer 240 and a patterned photoresist layer 250. The STI 210 is about 3000 Å to about 6000 Å deep. The thin dielectric layer 220 is about 10 Å to about 100 Å. The polysilicon is about 1000 Å to about 2000 Å. The DARC layer is about 200 Å to about 500 Å. The photoresist is about 2000 Å to about 3000 Å. The substrate 260 is ready to be placed in the plasma processing chamber for polysilicon (gate) etching.

When substrate 260 is placed in a processing chamber described in FIG. 1, an external light source 58 is applied to (shined on) the substrate 260 to allow the light to be reflected from the surface of the substrate 260. External light from broadband light source 58, e.g., a mercury, deuterium or xenon lamp, could be employed to provide light through fiber optic cable 54 to the wafer. The reflected light from the substrate surface is collected to determine a state of the substrate at any given time during processing. FIG. 2 shows different reflected light beams reflected from different interface layers, such as beam 271 reflected from the interface between the polysilicon 230 and the environment 260, beam 272 reflected from the interface between the polysilicon 230 and the thin dielectric 220, beam 273 reflected from the interface between the thin dielectric film 220 and substrate 200, beam 274 reflected from the interface between the STI 210 and substrate 200, beam 275 reflected from the interface between the photoresist 250 and DARC layer 240, and beam 276 reflected from the interface between the photoresist 250 and the environment 260. Different material layers would have their unique spectral reflectance characteristics. The phase shifts of the reflected light beams are affected by the thicknesses and refractive indices of the film materials on the substrate. These phase shifts allow the calculation and determination of the film thickness of these different layers, such as polysilicon layer 230, thin dielectric layers 220, depth of STI 210, and DARC layer 240, on the substrate 200. In addition to being affected by film thicknesses and materials of different films, the overall light reflectance, such includes intensity and phase shifts, from the substrate surface are also affected by the pattern density, critical dimensions of the patterns, and film qualities of the different layers on the substrate. Pattern density would affect the intensity of substrate reflectance. Wider or narrower pattern dimensions, such as photoresist 250 to photoresist 250 space dimension 264 and photoresist dimension 262, would affect the substrate reflectance intensity. Film quality would affect the refractive index of the film, which affect the phase shift and intensity of the substrate reflectance. If the photoresist patterning is mis-processed to have out of specification thickness or dimensions, comparing the substrate reflectance of the mis-processed substrate with the substrate reflectance of "normal" (or reference) substrates would reveal the abnormality.

Principle component analysis (PCA) is a multivariate technique which transforms a number of correlated variables to a smaller set of uncorrelated variables or factors that describe the major variation in a data set. An example of data matrix $X_{mn}$ is composed of m samples (rows), taken at $t_1$, $t_2$ to $t_m$, and n variables (columns), such as reflected light intensities at various wavelengths. An example of the reflected light monitoring by EyeD™ product of Applied Materials, which includes 1201 reflected light data channels (between 200 to 800 nm wavelengths). The signals can be sampled once per substrate prior to substrate processing or at 10 times per second during substrate processing. The columns of $X_{mn}$ are usually normalized to zero mean and unit variance.

$$X_{mn} = \begin{vmatrix} X_{11} & X_{12} & \ldots & X_{1n} \\ X_{21} & X_{22} & \ldots & X_{2n} \\ \vdots & \vdots & & \vdots \\ X_{m1} & X_{m2} & \ldots & X_{mn} \end{vmatrix} \quad (1)$$

Principle components (PCs) are the eigenvectors of matrix $X^T X$ (here $X=X_{mn}$).

$$X^T X = V \Omega V^T \quad (2)$$

The columns of V are the eigenvectors and the diagonal elements of $\Omega$ are the eigenvalues. The technique capitalizes on the fact that very often many parameters are correlated. The PC vectors (eigenvectors) are ordered by their eigenvalues. Typically, the first two PC vectors capture more than 90% of the variations in signals, therefore, minimizing the dimensionality of the system.

The data matrix $X_{mn}$ can be decomposed into a score matrix T (orthogonal) and a loading matrix P (orthonormal) plus a residual matrix E. The score matrix contains information on how the samples related to one another, while the loading matrix contains information on how variables related to one another.

$$X_{mn} = T_{ml} P^T_{nl} + E_{mn} \quad (3)$$

The abnormal changes in a sample can be detected by monitoring its scores and the values of the sum of squares of each row of E (residual matrix) (called Q) and the sum of the normalized squared scores (called $T^2$).

Figure 3:
FIG. 3 shows a graphical output data from an optical spectrometer.

Utilizing PCA, abnormal changes in a sample (or substrate) can be detected. Prior to substrate processing, the substrate reflectance of the substrate under study can be compared to the substrate reflectance of reference substrates to determine if the thicknesses of the films, qualities of the films, and/or the dimensions on the substrate are within the control limits or show abnormalities. The substrate reflectance data are collected in a particular instant $t_i$, since prior to processing the substrate reflectance does not change with time. The reflectance wavelength range monitored can be selected to fit the need of particular application. Typically, the wavelength range monitored is between about 200 nm to about 800 nm. FIG. 3 shows an exemplary graph of the substrate reflectance taken at $t_i$. The intensities at different wavelengths would be the data at a particular row of data matrix $X_{mn}$ in equation (1). The other rows are filled with data from reference substrates or from previous "normal" (or good) production substrates. PCA on the data matrix would be able to determine if the substrate under study falls in the normal limits. PCA is only an exemplary multi-variant analysis (MVA) technique; other applicable multi-variant analysis techniques can also be used.

Figure 4:
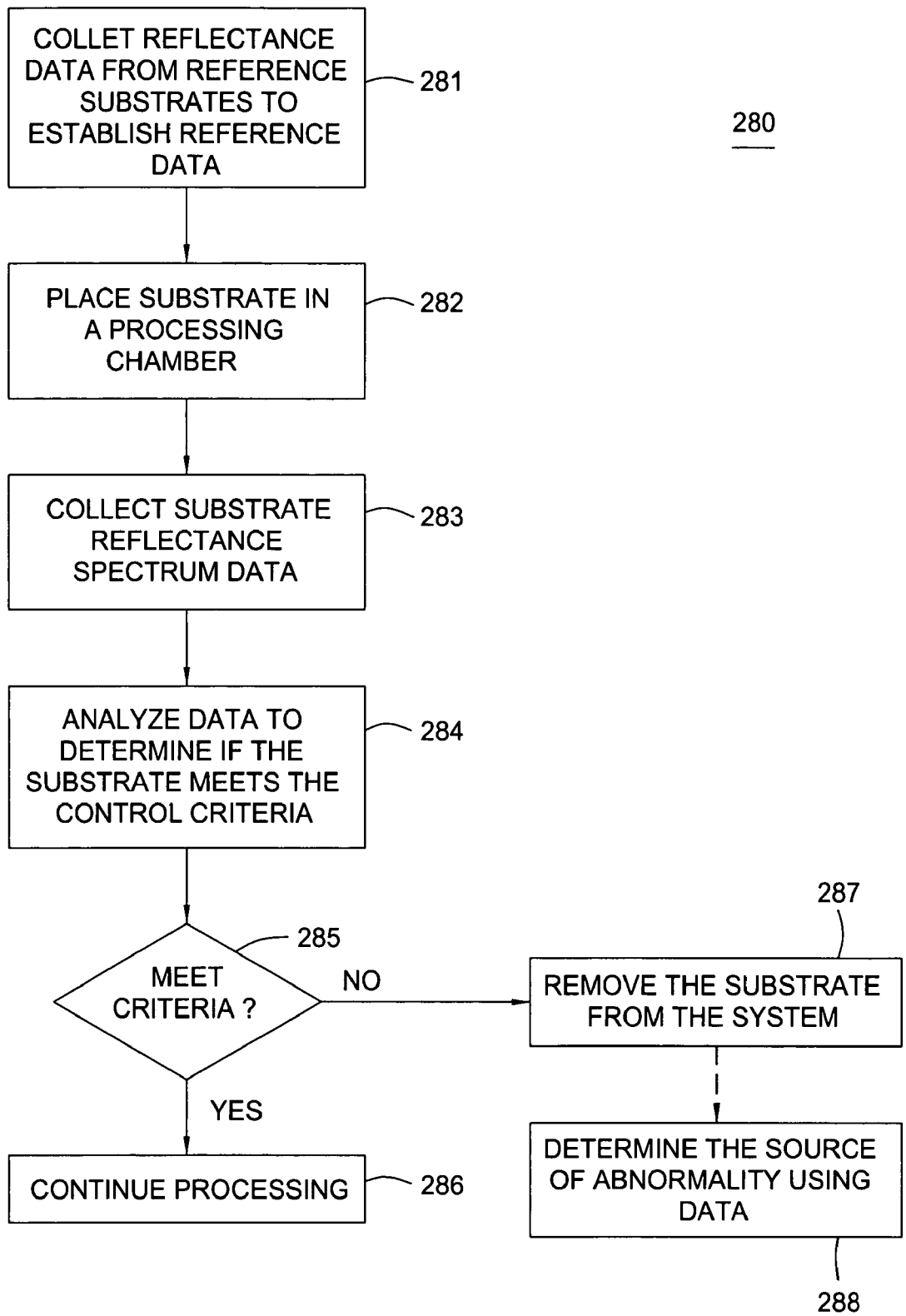
FIG. 4 shows a process of evaluating the state of a substrate in a process chamber prior to processing.

FIG. 4 shows the process flow 280 of monitoring the incoming substrates for abnormalities. At step 281, reflectance data of reference substrates is collected to store as part of a data matrix for multivariable analysis (MVA) analysis, such as PCA. Reference substrates are known "good" substrates that have been processed with the same process sequence as the substrate under study. At step 282, a substrate is placed in the processing chamber. At step 283, an external light is shined on the substrate to allow the collection of substrate reflectance spectrum. At step 284, PCA analysis is conducted on the data collected at step 283 along with data collected in step 281. The abnormality in the substrate under study can be detected by monitoring its scores and the values of the sum of squares of each row of E (residual matrix) (called Q) and the sum of the normalized squared scores (called $T^2$). At step 285, the sum of squares each row of E (or Q) and the sum of normalized squares ($T^2$) are compared against the passing criteria to determine if the substrate has met the incoming material screening criteria that is considered "normal". If the substrate meets the criteria, it can be processed in the chamber at step 286. If the substrate does not meet the criteria, it will be removed from the system at step 287. The spectrum of the substrate under study can be further analyzed to trace the source of abnormality at step 288. A design of experiment (DOE) can be conducted to build a data library to help identify the source of different abnormality (or fault classification). Spectra with known source of abnormalities can also be added to the data library to help identify the source of different abnormality (or fault classification).

Some abnormalities in the substrate might not have been detected during pre-processing screening. These abnormalities could be revealed during processing. During processing, reflected spectrum is continuously collected to be analyzed. The time dependent change of wafer reflectance represents the wafer response to the process plasma, which is a very sensitive indicator of process health and process consistency from substrate to substrate. Additional substrate state and process state information could be revealed by the data analysis of reflected spectrum collected during substrate processing. Polysilicon etch of the film stack shown in FIG. 2 can be used as an example. Polysilicon etch for the structure shown in FIG. 2 may include three process steps. The first etch is a main etch to generate a poly gate profile, the second etch is a soft landing etch with low bias power and high poly to oxide (thin dielectric layer 220) selectivity, and the third etch is an over etch to remove all polysilicon stringers on the substrate. During polysilicon etching, substrate reflectance is collected as a function of time. The collected data is analyzed to detect any abnormality of the substrate. The abnormality of the substrate could be a result of abnormality within the substrate prior to etch or could be a result of etch process abnormality, such as process drift.

FIG. 5 shows the process flow 300 of such a detection process. Process flow 300 starts at step 301 by first collecting reflectance data from reference substrates in reference chamber(s) during processing to establish reference data. At step 302, a substrate is placed in a processing chamber. At step 303, the poly etching process and reflectance data collection are started. Typically, the substrate reflectance data collection is started after the poly etch is started. The reflected optical spectrum is collected as a function of time, such as 10 times per second. At step 304, the etch process and substrate reflectance data collection are ended. At step 305, data analysis is conducted to determine if the substrate shows any abnormality resulting from incoming substrate or from etch processing. The data analyzed is data collected during the current run at step 303 together with reference data collected at step 301. At step 306, the system decides whether the substrate under study is the last substrate for the system to be studied. If the answer is yes, the process is ended at step 307. If the answer is no, the process flow returns to step 302 to place another substrate in the processing chamber. The data analysis of step 305 can also occur after step 306 or step 307, but preferably before step 306 to identify abnormal etch processing of the processing system under study.

Figure 6A:
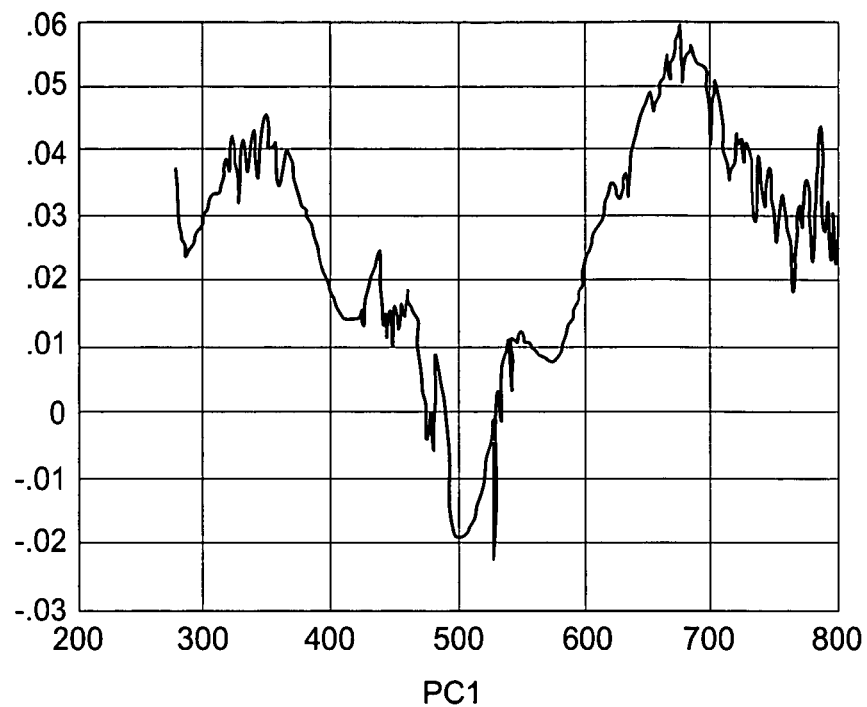
FIGS. 6A and 6B show the PC1 and PC2 identified from data analysis of a polysilicon etch.
Figure 6B:
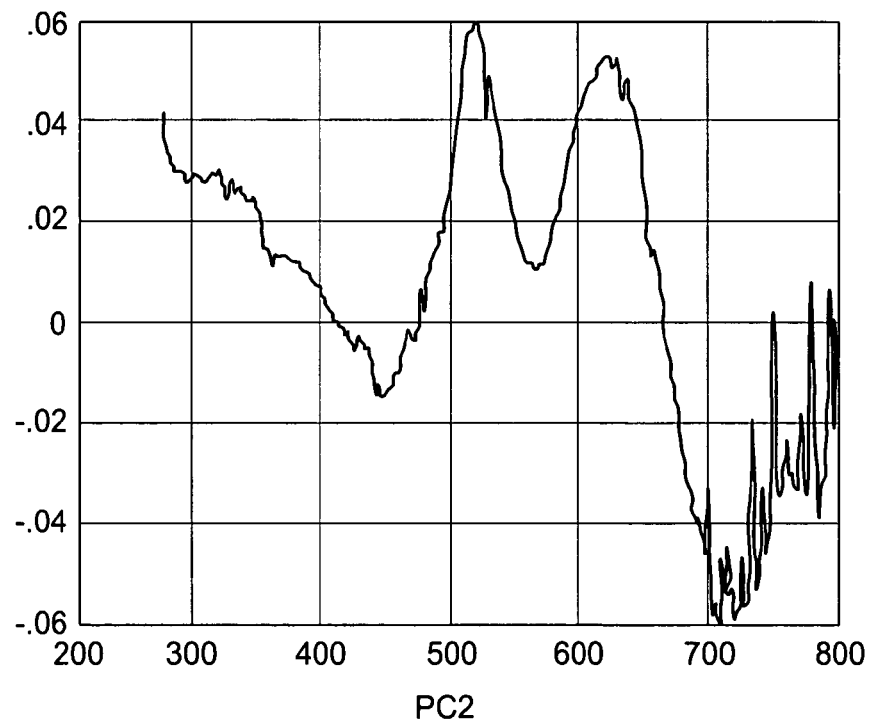

Following is an example of substrate abnormalities detected by analyzing substrate reflectance data collected during the main etch step. Of the three polysilicon etch steps, main etch step reveals most about the quality, thickness and dimensions of the polysilicon layer. The polysilicon etch process is conducted in a DPSII chamber (described below). The main etch is performed under 12 mTorr, 400 watts source power, 80 watts bias power, 80 sccm $Cl_2$, 80 sccm HBr and 10 sccm $CF_4$. For a polysilicon thickness of 1200 Å, roughly 1000 Å of polysilicon is etched during the main etch step. FIGS. 6A and 6B show two principle components identified, PC1 and PC2. PC1 mainly identifies changes of wavelength between 425 nm to 550 nm, which reflects the quality and thickness of the polysilicon layer. PC2 mainly identifies changes of wavelength between 500 nm to 700 nm, which reflects the quality and thickness of the STI layer.

Figure 7A:
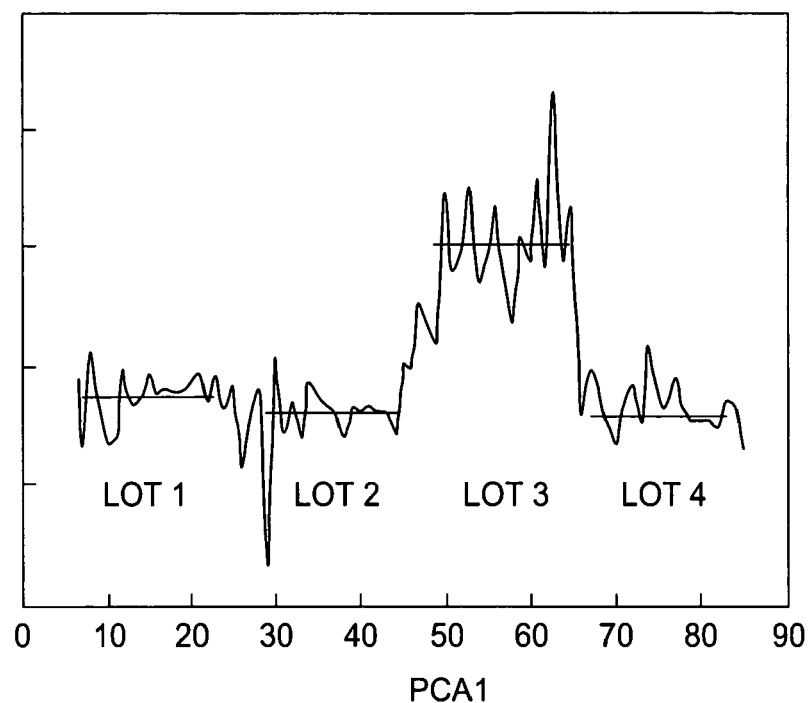
FIGS. 7A and 7B show principle component (PC) scores of 4 lots that went through substrate reflectance data analysis.
Figure 7B:
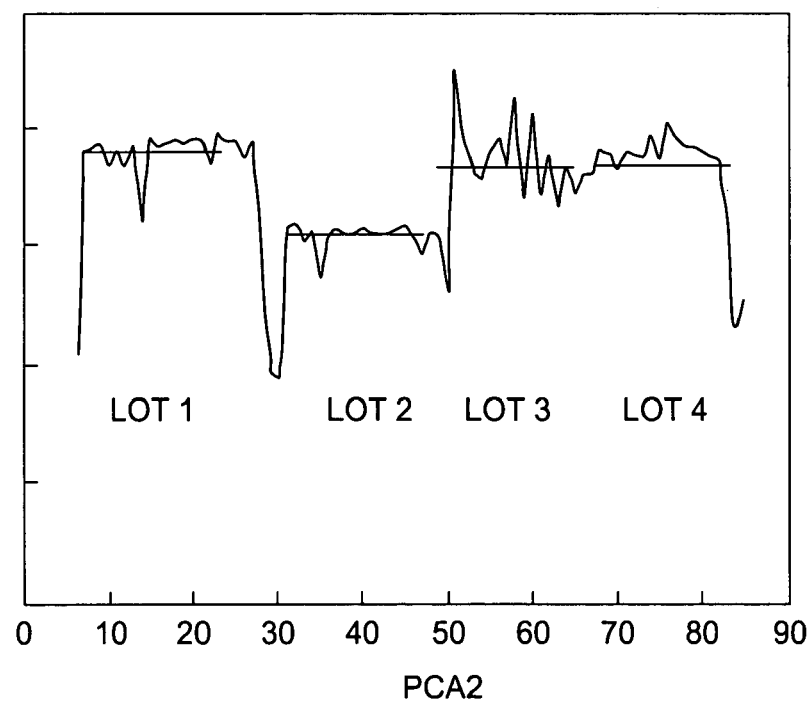

FIGS. 7A and 7B show the PC scores of 4 lots collected during the main etch process step. In FIG. 7A, Lot 3 shows higher PC1 scores compared to lots 1, 2 and 4, suggesting an abnormal incoming polysilicon layer in lot 3. The abnormality of lot 3 is later confirmed by data analysis to show the polysilicon thickness of lot 3 is thicker than lots 1, 2, and 4. In FIG. 7B, Lot 2 shows lower PC2 scores compared to lots 1, 3 and 4, which suggests an abnormal incoming STI layer for lot 2. Analysis afterwards shows that the STI thickness (or depth) is thinner for lot 2, compared to lots 1, 3, and 4. Thicker polysilicon layer could potentially affect polysilicon (or gate) CDs and therefore the device performance. The impact of slightly thinner (or shallower) STI is not as obvious; however, if the STI is too thin (or too shallow), its device isolation capability could be affected. The abnormalities of the polysilicon layer of lot 3 and STI layer of lot 2 can be used to check for abnormalities in systems used for polysilicon deposition, STI etch, STI fill and STI chemical-mechanical polishing (CMP). For advanced manufacturing, it is important to identify process abnormalities. Early detection of out of specification substrates could save manufacturing resources and early identification of system or process abnormality can prevent further loss of substrates.

Although the results in FIGS. 7A and 7B are used to identify problems with substrate on a lot to lot level, the method can be used to identify problems with substrate on a wafer to wafer level. The concept and apparatus of detecting problems with substrates before processing and during processing with in-situ substrate reflectance collection and analysis devices can be used for any processing system. The pre-measurement before substrate processing and measurement during substrate processing to detect problems can also be applied on the same substrate. If the processing system is a plasma processing system, the substrate reflectance could be just from the plasma light of the process or the plasma light in conjunction with external light sources. For non-plasma process, external light source(s) would need to be used. In addition to semiconductor substrate processing, the concept of the invention can also be applied to processing systems for flat panel displays.

Figure 8:
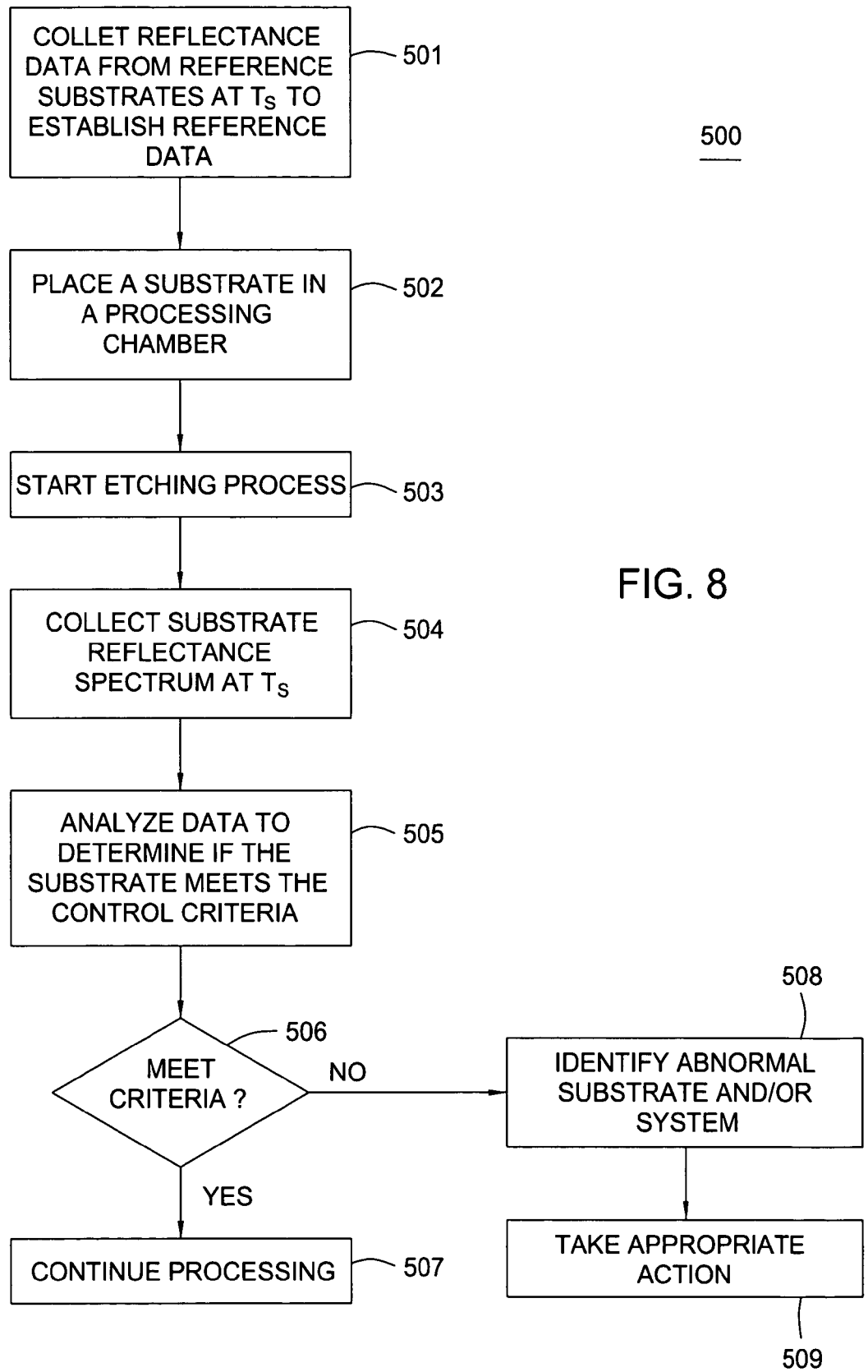
FIG. 8 show a process of evaluating the state of a substrate in a process chamber during processing.

The method described in FIG. 4, to check the normality of substrate prior to substrate processing, can also be used during substrate processing. Substrate reflectance taken at specific time, $t_s$, can be compared to reference data to check for its normality. FIG. 8 shows the process flow 500 of such a process. At step 501, substrate reflectance of reference substrates are collected at a specific time, $t_s$, during etching process to store as part of a data matrix for multivariable analysis (MVA) analysis, such as PCA. At step 502, a substrate is placed in the processing chamber. At step 503, the etching process is started. At step 504, the substrate reflectance spectrum data is collected at a specific time, $t_s$. The substrate reflectance spectrum data can be collected at multiple specific time, $t_{s1}$, $t_{s2}$, $t_{s3}$, . . . etc, as long as there are reference data collected at identical $t_{s1}$, $t_{s2}$, $t_{s3}$, . . . etc, previously for data analysis. The light source for the substrate reflectance could be the plasma light or external light source as described earlier. At step 505, MVA analysis, such as PCA, is conducted on the data collected at step 504 along with data collected in step 501. The abnormality in the substrate, which could be caused by the abnormality of the processing system, under study can be detected by monitoring its scores and the values of the sum of squares of each row of E (residual matrix) (called Q) and the sum of the normalized squared scores (called $T^2$). At step 506, the sum of squares each row of E (or Q) and the sum of normalized squares ($T^2$) are compares against the passing criteria to determine if the substrate has passed the incoming material screening criteria to be considered "normal". If the substrate passes the criteria, processing can be continued in the chamber at step 508. If the substrate does not pass the criteria, the substrate and/or the system will be flagged to be "abnormal" at step 508. The reason the system could be flagged to be "abnormal" is that it is the potential cause of the substrate abnormality. Afterwards, appropriate action can be taken by the system or the operator at step 509, depending on the degree of abnormality and the system design. If the degree of abnormality is quite sever, the substrate can be scrapped and the system shut down for system fault analysis.

Figure 9:
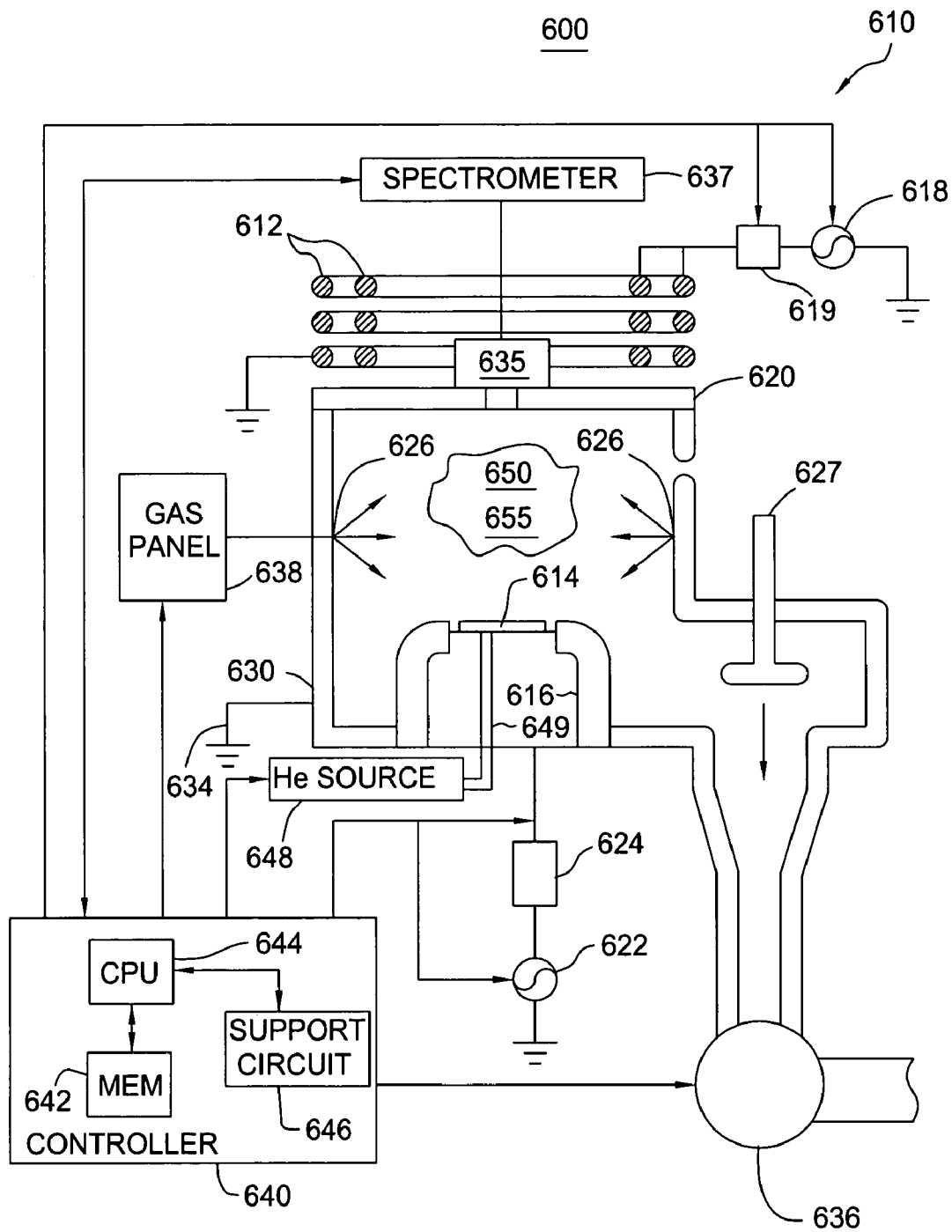
FIG. 9 is a schematic diagram of a DPS® II etch system adapted to operate in accordance with the present invention.

FIG. 9 depicts a schematic diagram of the exemplary Decoupled Plasma Source DPS® II etch reactor 600 that may be used to practice portions of the invention. The DPS® II reactor is generally used as a processing module of the CENTURA® processing system available from Applied Materials, Inc. of Santa Clara, Calif.

The reactor 600 comprises a process chamber 610 having a wafer support pedestal 616 within a conductive body (wall) 630, a beam-forming optics 635, a spectrometer 637, and a controller 640. The beam-forming optics 635 collect the reflectance from the substrate and the collected signals are sent to the spectrometer 637. The spectrometer 637 is connected to the controller 640. The substrate reflectance signals are analyzed by the spectrometer 637 and a processor 644 in the controller 644. The chamber could have be supplied with an optional external broadband light source (not shown) to provide light for substrate reflectance measurement. The chamber 610 is supplied with a substantially flat dielectric ceiling 620. Other modifications of the chamber 610 may have other types of ceilings, e.g., a dome-shaped ceiling. Above the ceiling 620 is disposed an antenna comprising at least one inductive coil element 612 (two co-axial elements 612 are shown). The inductive coil element 612 is coupled, through a first matching network 619, to a plasma power source 618. The plasma source 618 typically is capable of producing up to 3000 W at a tunable frequency in a range from 50 kHz to 13.56 MHz.

The support pedestal (cathode) 616 is coupled, through a second matching network 624, to a biasing power source 622. The biasing power source 622 generally is capable of producing up to 10 kW at a frequency of approximately 13.56 MHz.

The biasing power may be either continuous or pulsed power. In other embodiments, the biasing power source 622 may be a DC or pulsed DC source.

A controller 640 comprises a central processing unit (CPU) 644, a memory 642, and support circuits 646 for the CPU 644 and facilitates control of the components of the chamber 610 and, as such, of the etch process, as discussed.

In operation, a semiconductor wafer 614 is placed on the pedestal 616 and process gases are supplied from a gas panel 638 through entry ports 626 to form a gaseous mixture 650. The gaseous mixture 650 is ignited into a plasma 655 in the chamber 610 by applying power from the plasma source 618 and biasing source power 622 to the inductive coil element 612 and the cathode 616, respectively. The pressure within the interior of the chamber 610 is controlled using a throttle valve 627 and a vacuum pump 636. Typically, the chamber wall 630 is coupled to an electrical ground 634. The temperature of the wall 630 is controlled using liquid-containing conduits (not shown) that run through the wall 630.

The temperature of the wafer 614 is controlled by stabilizing a temperature of the support pedestal 616. In one embodiment, helium gas from a gas source 648 is provided via a gas conduit 649 to channels (not shown) formed in the pedestal surface under the wafer 614. The helium gas is used to facilitate heat transfer between the pedestal 616 and the wafer 614. During processing, the pedestal 616 may be heated by a resistive heater (not shown) within the pedestal to a steady state temperature and then the helium gas facilitates uniform heating of the wafer 614. Using such thermal control, the wafer 614 is maintained at a temperature between about 20 to 350 degrees Celsius.

Those skilled in the art will understand that other etch chambers may be used to practice the invention, including chambers with remote plasma sources, electron cyclotron resonance (ECR) plasma chambers, and the like.

To facilitate control of the process chamber 610 as described above, the controller 640 may be one of any form of general-purpose computer processor that can be used in an industrial setting for controlling various chambers and sub-processors. The memory 642, or computer-readable medium, of the CPU 644 may be one or more of readily available memory such as random access memory (RAM), read only memory (ROM), floppy disk, hard disk, or any other form of digital storage, local or remote. The support circuits 646 are coupled to the CPU 644 for supporting the processor in a conventional manner. These circuits include cache, power supplies, clock circuits, input/output circuitry and subsystems, and the like. The inventive method is generally stored in the memory 642 as a software routine. The software routine may also be stored and/or executed by a second CPU (not shown) that is remotely located from the hardware being controlled by the CPU 644.

Accordingly, while the present invention has been disclosed in connection with various embodiments thereof, it should be understood that other embodiments might fall within the spirit and scope of the invention, as defined by the following claims.

What is claimed is:

1. A method of evaluating a state of a substrate in a processing chamber, comprising:
    (a) collecting substrate reflectance data from at least one reference substrate to establish reference data;
    (b) placing a product substrate in a processing chamber;
    (c) collecting substrate reflectance spectrum data from the product substrate; and
    (d) analyzing the collected substrate reflectance and the substrate reflectance spectrum data to determine if a state of the product substrate meets a control criterion.

2. The method of claim 1, wherein steps (a), (b), (c) and (d) are performed prior to processing the product substrate.

3. The method of claim 1, wherein step (c) is performed during product substrate processing.

4. The method of claim 1, wherein step (c) is performed prior to and during processing the product substrate.

5. The method of claim 1, further comprising:
    applying, during step (c), an external broadband light to the product substrate.

6. The method of claim 5, wherein the external broadband light source is a mercury, deuterium or xenon lamp.

7. The method of claim 1, wherein the processing chamber is a plasma processing chamber.

8. The method of claim 1, wherein the substrate state is selected from film thicknesses, critical dimensions, film qualities, or a combination thereof.

9. The method of claim 1, wherein the control criterion is selected from the criteria for film thicknesses, critical dimensions, film qualities, or a combination thereof.

10. The method of claim 1, further comprising:
    identifying the product substrate that has a substrate state that does not meet the control criterion and the criteria that it does not pass.

11. The method of claim 10, further comprising:
    notifying an operator of the systems that potentially process the previously processed substrate to cause the substrate state to not meet the control criterion.

12. The method of claim 1, wherein the data analysis comprises multi-variant analysis.

13. The method of claim 12, wherein the multi-variant analysis comprises principle component analysis.

14. A method of evaluating a state of a substrate in an etch processing chamber, comprising:
    (a) collecting substrate reflectance data from at least one reference substrate to establish reference data;
    (b) placing a product substrate in an etch processing chamber;
    (c) collecting substrate reflectance spectrum data from the product substrate; and
    (d) analyzing collected the collected substrate reflectance and the substrate reflectance spectrum data to determine if a state of the product substrate meets a control criterion.

15. The method of claim 14, wherein steps (a), (b), (c) and (d) are performed prior to etching the product substrate.

16. The method of claim 14, wherein step (c) is performed during etch processing.

17. The method claim 14, wherein step (c) is performed prior to and during etch processing.

18. The method of claim 16, wherein the etch processing etches polysilicon.

19. The method of claim 17, wherein the etch processing etches polysilicon.

20. The method of claim 14, further comprising:
    applying, during step (c), an external broadband light to the product substrate.

21. The method of claim 20, wherein the external broadband light source is a mercury, deuterium or xenon lamp.

22. The method of claim 14, wherein the substrate state is selected from film thicknesses, critical dimensions, film qualities, or a combination thereof.

23. The method of claim 14, wherein the control criterion is selected from the criteria for film thicknesses, critical dimensions, film qualities, or a combination thereof.

24. The method of claim 14, further comprising:
    determining that the substrate state does not meet the control criterion and the criteria that the substrate state does not pass.

25. The method of claim 24, further comprising:
    notifying an operator of the systems that potentially cause the previously processed substrate to cause the substrate state to not meet the control criterion.

26. The method of claim 14, wherein the data analysis comprises multi-variant analysis.

27. The method of claim 26, wherein the multi-variant analysis comprises principle component analysis.

* * * * *

UNITED STATES PATENT AND TRADEMARK OFFICE
CERTIFICATE OF CORRECTION

| | | |
|---|---|---|
| PATENT NO. | : 7,393,459 B2 | Page 1 of 1 |
| APPLICATION NO. | : 10/939158 | |
| DATED | : July 1, 2008 | |
| INVENTOR(S) | : Davis et al. | |

It is certified that error appears in the above-identified patent and that said Letters Patent is hereby corrected as shown below:

In the Drawings

On sheet 4 of 9, in Fig. 4 (Reference Numeral 281), line 1, delete "COLLET" and insert -- COLLECT --, therefor.

On sheet 5 of 9, in Fig. 5 (Reference Numeral 301), line 1, delete "REFFECTANCE" and insert -- REFLECTANCE --, therefor.

On sheet 8 of 9, in Fig. 8 (Reference Numeral 501), line 1, delete "COLLET" and insert -- COLLECT --, therefor.

In column 3, line 14, delete "show" and insert -- shows --, therefor.

In column 8, line 10, delete "etc," and insert -- etc., --, therefor.

In column 10, line 47, in Claim 14, after "analyzing" delete "collected".

Signed and Sealed this

Twenty-fifth Day of November, 2008

JON W. DUDAS
*Director of the United States Patent and Trademark Office*